(12) United States Patent
Baruti et al.

(10) Patent No.: US 7,867,172 B1
(45) Date of Patent: Jan. 11, 2011

(54) COMBINATION TOOTHBRUSH AND PEAK FLOW METER SYSTEM

(76) Inventors: Dingane Baruti, 1126 Bank St., Bakersfield, CA (US) 93307; Mary A. Dean, 712 Union Ave., Bakersfield, CA (US) 93307

( * ) Notice: Subject to any disclaimer, the term of this patent is extended or adjusted under 35 U.S.C. 154(b) by 1098 days.

(21) Appl. No.: 11/558,118

(22) Filed: Nov. 9, 2006

(51) Int. Cl.
*A61B 5/08* (2006.01)

(52) U.S. Cl. ............... 600/538; 600/529; 600/531; 600/533; 600/539

(58) Field of Classification Search ......... 600/529–533, 600/538, 539, 540
See application file for complete search history.

(56) References Cited

U.S. PATENT DOCUMENTS

| | | | |
|---|---|---|---|
| 2,154,209 A | 4/1939 | Kohn | |
| 3,361,355 A | 1/1968 | Renee | |
| 4,538,631 A | 9/1985 | Prince | |
| 4,575,272 A | 3/1986 | Borrow | |
| D332,063 S | 12/1992 | Bellofatto et al. | |
| D332,229 S | 1/1993 | Brown | |
| 5,224,487 A | 7/1993 | Bellofatto et al. | |
| 5,228,166 A | 7/1993 | Gomez | |
| 5,373,851 A | 12/1994 | Reinhold, Jr. et al. | |
| 5,463,792 A | 11/1995 | Hogan et al. | |
| D366,221 S | 1/1996 | Cadera | |
| D367,433 S | 2/1996 | Helwig | |
| 5,540,234 A | 7/1996 | Lalui | |
| 5,561,881 A | 10/1996 | Klinger et al. | |
| 5,565,630 A | 10/1996 | Shene | |
| 5,613,497 A | 3/1997 | DeBush | |
| 5,627,324 A | 5/1997 | Shene | |
| 5,704,087 A | 1/1998 | Strub | |
| D394,016 S | 5/1998 | Bellofatto et al. | |
| 5,769,070 A | 6/1998 | Frati et al. | |
| 6,010,460 A | 1/2000 | McNaughton | |
| 6,079,075 A * | 6/2000 | Velez-Juan | 15/167.1 |
| 6,322,519 B1 * | 11/2001 | Moulin | 600/538 |
| 6,447,459 B1 | 9/2002 | Larom | |
| 6,485,300 B1 | 11/2002 | Muller et al. | |
| 6,632,091 B1 * | 10/2003 | Cise et al. | 433/116 |

FOREIGN PATENT DOCUMENTS

EP     0 634 151 A2     1/1995

* cited by examiner

*Primary Examiner*—Charles A Marmor, II
*Assistant Examiner*—Michael D'Angelo
(74) *Attorney, Agent, or Firm*—Michael S. Neustel

(57) ABSTRACT

A combination toothbrush and peak flow meter system for increasing the compliance of peak flow measurements in children and adults with asthma. The combination toothbrush and peak flow meter system includes a peak flow meter and a toothbrush head connected to an end of the peak flow meter.

20 Claims, 6 Drawing Sheets

COMBINATION TOOTHBRUSH AND PEAK FLOW METER SYSTEM

CROSS REFERENCE TO RELATED APPLICATIONS

Not applicable to this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to peak flow meters and more specifically it relates to a combination toothbrush and peak flow meter system for increasing the compliance of peak flow measurements in children and adults with asthma.

2. Description of the Related Art

Any discussion of the prior art throughout the specification should in no way be considered as an admission that such prior art is widely known or forms part of common general knowledge in the field.

Peak flow meters have been in use for years for measuring the maximum velocity of exhaled air. Peak flow meters are typically comprised of a portable device that provides a digital or analog readout of the measured peak flow rate (usually measured in liters per minute). The peak flow rate measurements are used for assessing lung functionality in asthmatic children. A child with asthma utilizes a peak flow meter by blowing into an intake port as hard as they can. It is preferable to repeat the measurement test at least 3 times with the highest reading recorded. It is further preferable that the measurements occur at the same time of each day to provide an accurate comparison basis. Medical professionals are able to monitor and modify medical treatment for a patient based in part on the readings from the peak flow meters.

The main problem with peak flow meters is that children often times forget to take their daily readings. With reduced frequency of usage of a peak flow meter, there is the potential for a delayed warning of declining pulmonary function.

While these devices may be suitable for the particular purpose to which they address, they are not as suitable for increasing the compliance of peak flow measurements in children with asthma. Conventional peak flow meters are often times not frequently used and can be misplaced due in part because of infrequent usage.

In these respects, the combination toothbrush and peak flow meter system according to the present invention substantially departs from the conventional concepts and designs of the prior art, and in so doing provides an apparatus primarily developed for the purpose of increasing the compliance of peak flow measurements in children and adults with asthma.

BRIEF SUMMARY OF THE INVENTION

In view of the foregoing disadvantages inherent in the known types of peak flow meters now present in the prior art, the present invention provides a new combination toothbrush and peak flow meter system construction wherein the same can be utilized for increasing the compliance of peak flow measurements in children with asthma.

The general purpose of the present invention, which will be described subsequently in greater detail, is to provide a new combination toothbrush and peak flow meter system that has many of the advantages of the peak flow meters mentioned heretofore and many novel features that result in a new combination toothbrush and peak flow meter system which is not anticipated, rendered obvious, suggested, or even implied by any of the prior art peak flow meters, either alone or in any combination thereof. To attain this, the present invention generally comprises a peak flow meter and a toothbrush head connected to an end of the peak flow meter.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a combination toothbrush and peak flow meter system that will overcome the shortcomings of the prior art devices.

A second object is to provide a combination toothbrush and peak flow meter system for increasing the compliance of peak flow measurements in children and adults with asthma.

Another object is to provide a combination toothbrush and peak flow meter system that assists in providing advanced warning of declining pulmonary function.

An additional object is to provide a combination toothbrush and peak flow meter system that encourages frequent and periodic usage of a peak flow meter.

A further object is to provide a combination toothbrush and peak flow meter system that encourages the usage of a peak flow meter during the morning when an asthma patient brushes their teeth.

Another object is to provide a combination toothbrush and peak flow meter system that is usable by children and adults.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Figure 1:
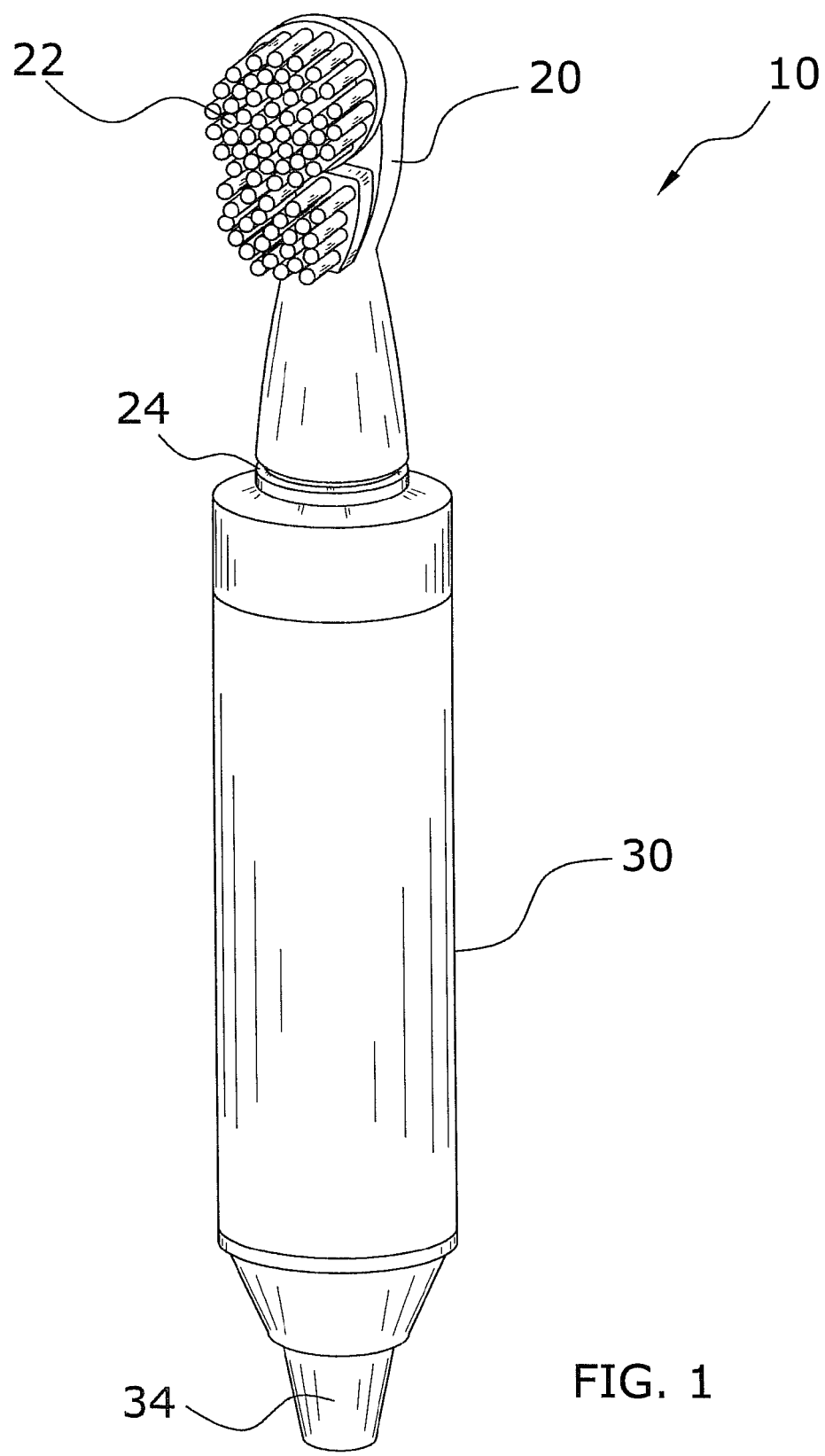
FIG. 1 is an upper perspective view of the present invention.

Turning now descriptively to the drawings, in which similar reference characters denote similar elements throughout the several views, FIGS. 1 through 6 illustrate a combination toothbrush and peak flow meter system 10, which comprises a peak flow meter 30 and a toothbrush head 20 connected to an end of the peak flow meter 30.

B. Peak Flow Meter

The peak flow meter 30 may be comprised of any device capable of measuring a peak flow rate of a user suffering from asthma. The peak flow meter 30 is preferably comprised of a digital flow meter device with a digital display 38 to show the measured flow rate which are well known in the art. The measured flow rate is preferably shown in liters per minute, however other measured units may be utilized. The peak flow meter 30 may also be comprised of a mechanical analog structure which utilizes a mechanical measuring indicator to show the peak flow rate. The peak flow meter 30 includes an intake port 34 and an exit port 36 that allows the user to blow through.

Figure 3:
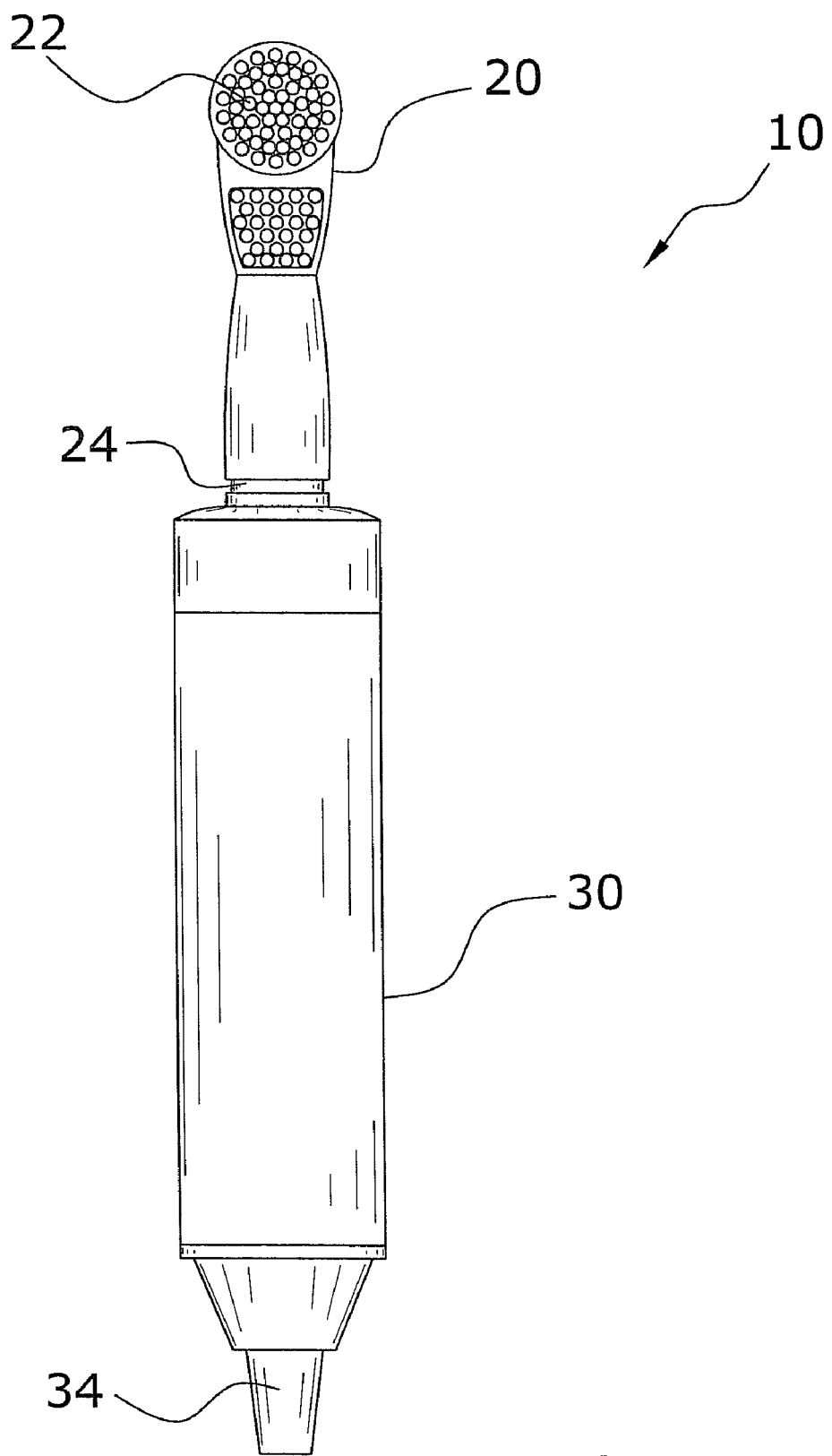
FIG. 3 is a front view of the present invention illustrating the toothbrush head.
Figure 4:
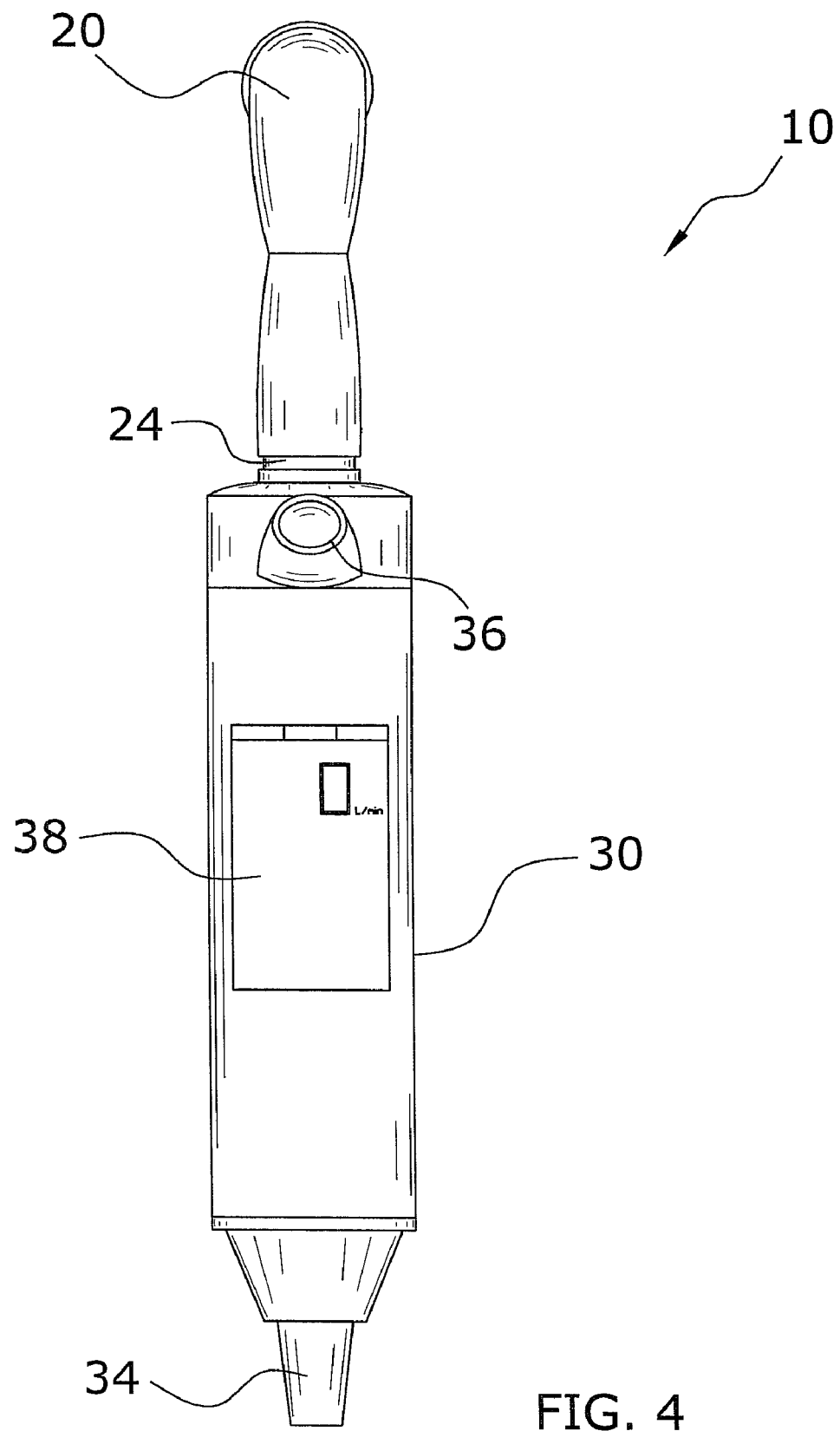
FIG. 4 is a rear view of the present invention illustrating the display of the peak flow meter.
Figure 5:
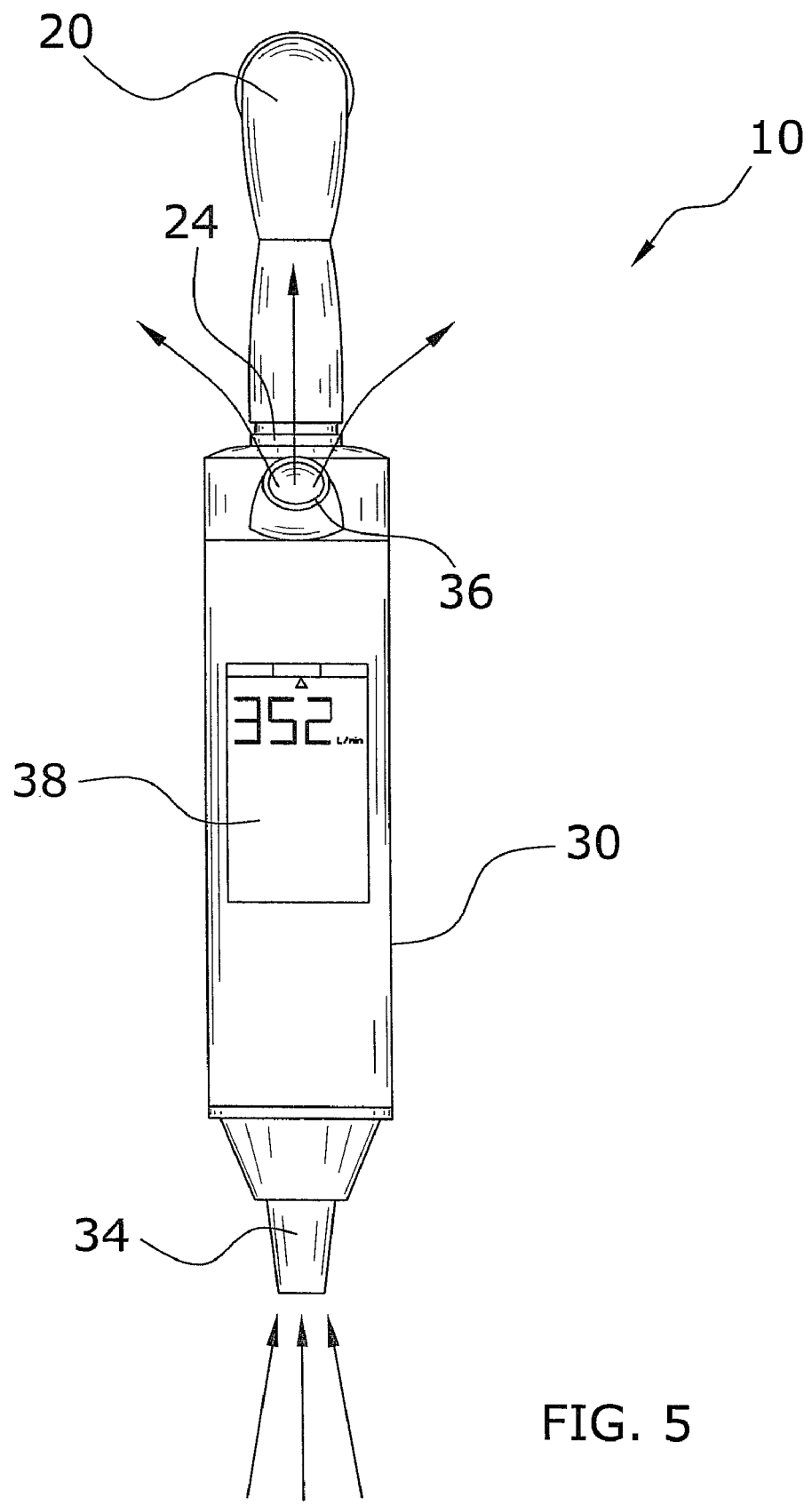
FIG. 5 is a rear view of the present invention illustrating a peak flow rate measurement because of airflow input into the peak flow meter.
Figure 6:
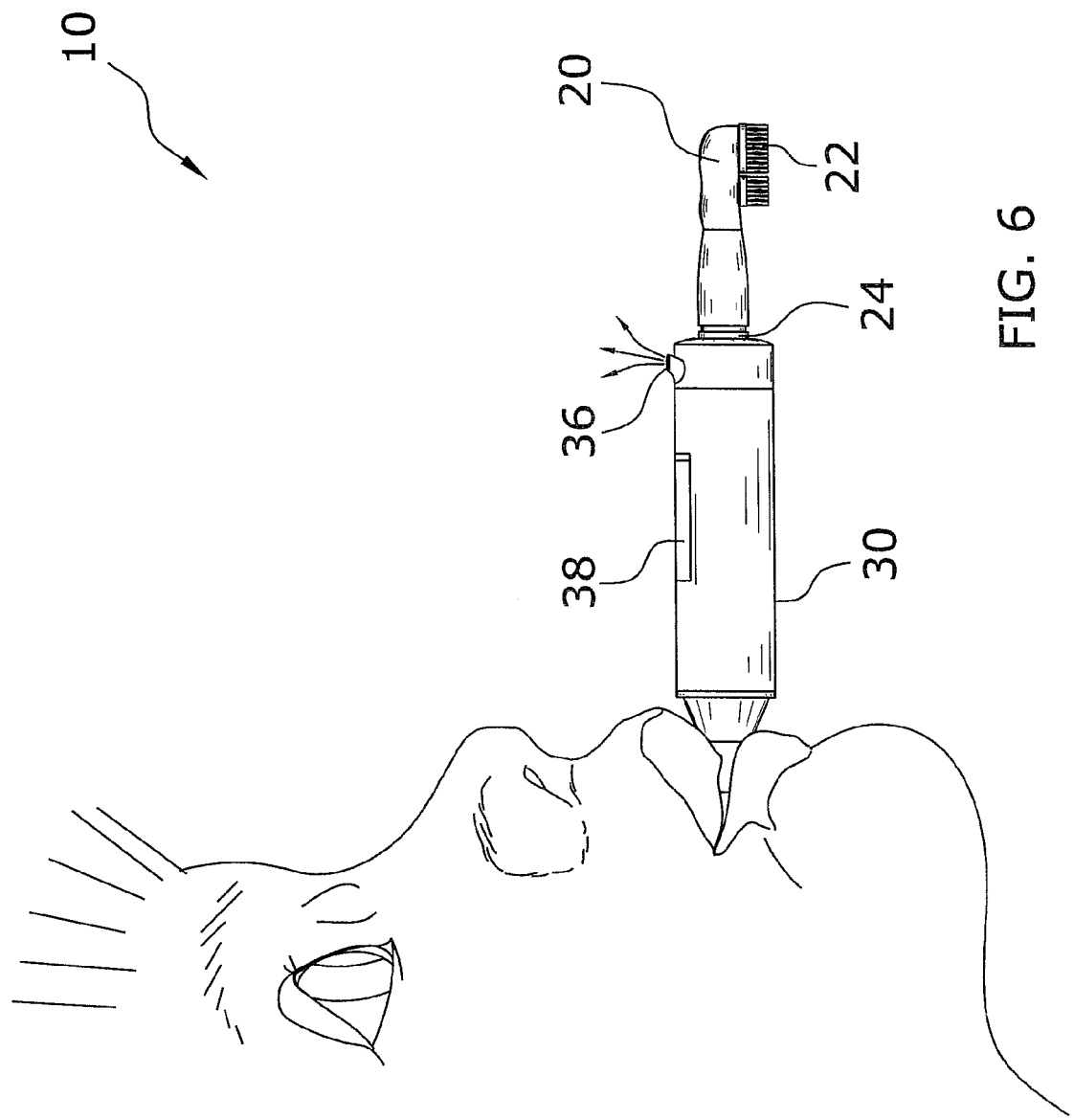
FIG. 6 is a side view of the present invention with the intake port being blown into by an individual.

The user positions their lips about the intake port 34 as shown in FIG. 6 and blows a burst of air through the intake port 34 which is then exhausted out the exit port 36 away from the bristles 22 of the toothbrush to avoid contamination of the bristles 22. The intake port 34 is preferably comprised of an elongated and tapering structure as best illustrated in FIGS. 3 through 5 of the drawings. The intake port 34 is preferably concentrically positioned with respect to the body of the peak flow meter 30. The intake port 34 is preferably positioned opposite of the toothbrush head 20 as best illustrated in FIG. 3 of the drawings.

The exit port 36 is preferably directed rearwardly and away from the user to direct the flow of the air exiting away from the user and away from the toothbrush head 20. The exit port 36 preferably extends a finite distance beyond the body of the peak flow meter 30 as shown in FIGS. 3 through 6 of the drawings.

The peak flow meter 30 includes a first connecting end 24 that receives the toothbrush head 20 in removable or non-removable manner. The peak flow meter 30 is preferably comprised of an elongated structure to provide a handle for the user to grasp when brushing their teeth with the toothbrush head 20.

C. Toothbrush

Figure 2:
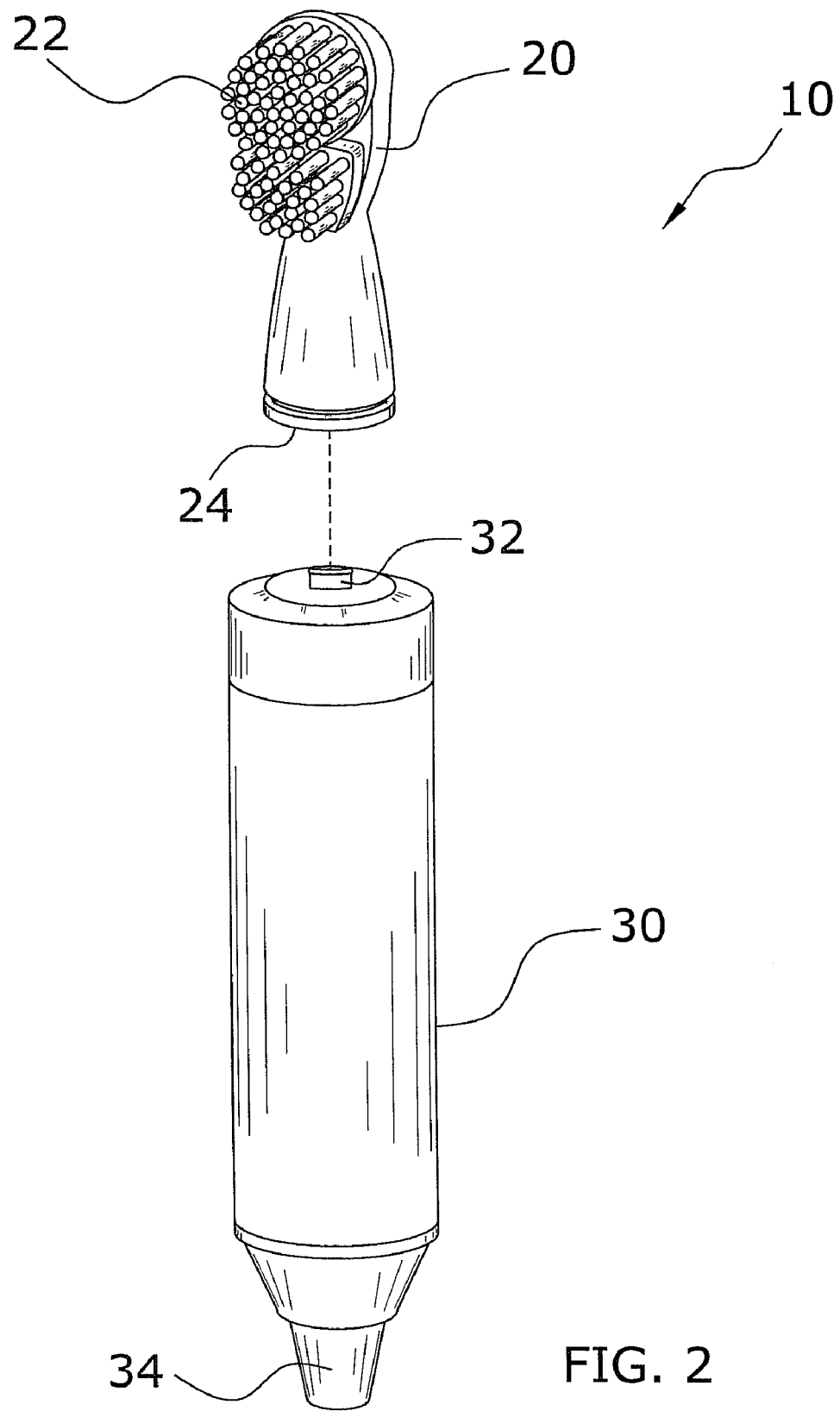
FIG. 2 is an exploded upper perspective view of the present invention.

The toothbrush head 20 includes a first connecting end 24 that attaches to the second connecting end 32 of the peak flow meter 30 as shown in FIG. 2 of the drawings. The second connecting end 32 is preferably detachably connected to the first connecting end 24 of the peak flow meter 30 to allow for replacement of the toothbrush head 20 after it has become worn or damaged. The first connecting end 24 and the second connecting end 32 are comprised of interlocking fasteners that allow for snapping of the toothbrush head 20 to the body of the peak flow meter 30. The toothbrush head 20 is preferably concentrically attached to the peak flow meter 30 to provide for a uniform and balanced brushing of the teeth of the user.

The toothbrush head 20 includes a plurality of bristles 22 as best illustrated in FIGS. 1 through 3 of the drawings. The plurality of bristles 22 preferably extend forwardly from the toothbrush head 20 in a direction opposite of the air flow from the exit port 36 as shown in FIG. 6 of the drawings. The toothbrush head 20 preferably includes a narrow and tapered neck portion similar to conventional toothbrushes.

D. Operation of Invention

In use, the user is able to utilize the toothbrush head 20 as a toothbrush to brush their teeth as they normally would operate a toothbrush (not illustrated). After or before brushing their teeth, the user would utilize the peak flow meter 30 of the present invention to measure the peak flow rate of the user. Because the peak flow meter 30 is connected to the toothbrush head 20 the user is reminded to utilize the peak flow meter 30 when they brush their teeth. In addition, it is relatively easy to utilize the peak flow meter 30 after or before brushing their teeth since the peak flow meter 30 is readily available from brushing the user's teeth.

What has been described and illustrated herein is a preferred embodiment of the invention along with some of its variations. The terms, descriptions and figures used herein are set forth by way of illustration only and are not meant as limitations. Those skilled in the art will recognize that many variations are possible within the spirit and scope of the invention, which is intended to be defined by the following claims (and their equivalents) in which all terms are meant in their broadest reasonable sense unless otherwise indicated. Any headings utilized within the description are for convenience only and have no legal or limiting effect.

We claim:

1. A combination toothbrush and peak flow meter system, comprising:
    a peak flow meter to measure a peak flow rate, wherein said peak flow meter includes an intake port and an exit port; and
    a toothbrush head connected to an end of said peak flow meter, wherein said toothbrush head includes a plurality of bristles.

2. The combination toothbrush and peak flow meter system of claim 1, wherein said toothbrush head is concentrically attached to said peak flow meter.

3. The combination toothbrush and peak flow meter system of claim 1, wherein said exit port extends rearwardly from a rear portion of said peak flow meter.

4. The combination toothbrush and peak flow meter system of claim 3, wherein said plurality of bristles of said toothbrush head extend forwardly from a front portion of said toothbrush head.

5. The combination toothbrush and peak flow meter system of claim 1, wherein said intake port is positioned opposite of said toothbrush head.

6. The combination toothbrush and peak flow meter system of claim 1, wherein said peak flow meter is comprised of a digital unit.

7. The combination toothbrush and peak flow meter system of claim 6, wherein said peak flow meter includes a display to show a measured peak flow rate.

8. The combination toothbrush and peak flow meter system of claim 1, wherein said peak flow meter is comprised of a mechanical analog unit.

9. The combination toothbrush and peak flow meter system of claim 1, wherein said toothbrush head includes a neck portion.

10. The combination toothbrush and peak flow meter system of claim 1, wherein said peak flow meter is comprised of an elongated structure.

11. A combination toothbrush and peak flow meter system, comprising:
   a peak flow meter to measure a peak flow rate, wherein said peak flow meter includes an intake port, an exit port and a second connecting end, and wherein said peak flow meter is comprised of an elongated structure; and
   a toothbrush head including a first connecting end, wherein said second connecting end is detachably connected to said first connecting end of said toothbrush head, wherein said toothbrush head includes a plurality of bristles.

12. The combination toothbrush and peak flow meter system of claim 11, wherein said toothbrush head is concentrically attached to said peak flow meter.

13. The combination toothbrush and peak flow meter system of claim 11, wherein said exit port extends rearwardly from a rear portion of said peak flow meter.

14. The combination toothbrush and peak flow meter system of claim 13, wherein said plurality of bristles of said toothbrush head extend forwardly from a front portion of said toothbrush head.

15. The combination toothbrush and peak flow meter system of claim 11, wherein said intake port is positioned opposite of said toothbrush head.

16. The combination toothbrush and peak flow meter system of claim 11, wherein said peak flow meter is comprised of a digital unit and wherein said peak flow meter includes a display to show a measured peak flow rate.

17. The combination toothbrush and peak flow meter system of claim 11, wherein said peak flow meter is comprised of a mechanical analog unit.

18. The combination toothbrush and peak flow meter system of claim 11, wherein said toothbrush head includes a neck portion.

19. The combination toothbrush and peak flow meter system of claim 11, wherein said first connecting end and said second connecting end are comprised of interlocking fasteners.

20. A combination toothbrush and peak flow meter system, comprising:
   a peak flow meter to measure a peak flow rate, wherein said peak flow meter includes an intake port, an exit port and a second connecting end, and wherein said peak flow meter is comprised of an elongated structure;
   wherein said exit port extends rearwardly from a rear portion of said peak flow meter;
   wherein said intake port is positioned opposite of said toothbrush head;
   wherein said peak flow meter is comprised of a digital unit and wherein said peak flow meter includes a display to show a measured peak flow rate; and
   a toothbrush head including a first connecting end, wherein said second connecting end is detachably connected to said first connecting end of said toothbrush head, wherein said toothbrush head includes a plurality of bristles;
   wherein said toothbrush head includes a neck portion;
   wherein said toothbrush head is concentrically attached to said peak flow meter;
   wherein said plurality of bristles of said toothbrush head extend forwardly from a front portion of said toothbrush head;
   wherein said first connecting end and said second connecting end are comprised of interlocking fasteners.

\* \* \* \* \*